US008447384B2

(12) United States Patent
Xu et al.

(10) Patent No.: US 8,447,384 B2
(45) Date of Patent: May 21, 2013

(54) METHOD AND SYSTEM FOR PERFORMING BIOPSIES

(75) Inventors: Sheng Xu, Rockville, MD (US); Jochen Kruecker, Washington, DC (US); Guy Shechter, Briarcliff Manor, NY (US); Ian Farmer, Capitola, CA (US); Peter Lyle Choyke, Bethesda, MD (US); Peter Pinto, Bethesda, MD (US); Bradford J. Wood, Potomac, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 52 days.

(21) Appl. No.: 12/993,854

(22) PCT Filed: Jun. 12, 2009

(86) PCT No.: PCT/IB2009/052519
§ 371 (c)(1),
(2), (4) Date: Nov. 22, 2010

(87) PCT Pub. No.: WO2009/153723
PCT Pub. Date: Dec. 23, 2009

(65) Prior Publication Data
US 2011/0082363 A1 Apr. 7, 2011

Related U.S. Application Data (60) Provisional application No. 61/074,158, filed on Jun. 20, 2008.

(51) Int. Cl.
*A61B 5/05* (2006.01)

(52) U.S. Cl.
USPC .......................................... 600/429; 606/130

(58) Field of Classification Search
USPC .................. 600/407–429, 437–469; 606/130
See application file for complete search history.

(56) References Cited

U.S. PATENT DOCUMENTS 6,238,342 B1    5/2001  Feleppa et al.
7,697,972 B2 *  4/2010  Verard et al. .................. 600/424
(Continued)

FOREIGN PATENT DOCUMENTS

EP    1323380     7/2003
EP    1720039    11/2006
(Continued)

OTHER PUBLICATIONS

Yiqiang Zhan et al., "Registering Histologic and MR Images of Prostate for Image-Based Cancer Detection", Acad Radiol 2007; 14: 1367-1381.
(Continued)

*Primary Examiner* — Sanjay Cattungal (57) ABSTRACT

A method and system for performing biopsies can include an imaging system for obtaining diagnostic images of a target region; a tracking system; a probe having a deployable biopsy needle for performing a biopsy procedure where the tracking system generates tracking information for at least one of the probe and the biopsy needle; an ultrasound imaging system for obtaining ultrasound imaging of the target region; and a computer in communication with the tracking system, the imaging system and the ultrasound imaging system. The computer can register the tracking system with the imaging system. The computer transfers a marking of a biopsy site associated with the biopsy procedure from the ultrasound imaging to the diagnostic images based on the tracking information and the registration of the tracking system with the diagnostic images.

20 Claims, 11 Drawing Sheets

U.S. PATENT DOCUMENTS

| | | | |
|---|---|---|---|
| 7,831,293 B2 * | 11/2010 | Ellis et al. | 600/424 |
| 8,000,773 B2 * | 8/2011 | Rousso et al. | 600/436 |
| 2003/0210812 A1 | 11/2003 | Khamene et al. | |
| 2004/0009459 A1 * | 1/2004 | Anderson et al. | 434/262 |
| 2005/0054910 A1 * | 3/2005 | Tremblay et al. | 600/411 |
| 2005/0182319 A1 * | 8/2005 | Glossop | 600/424 |
| 2006/0241368 A1 * | 10/2006 | Fichtinger et al. | 600/407 |
| 2007/0038058 A1 * | 2/2007 | West et al. | 600/407 |
| 2010/0286517 A1 * | 11/2010 | Kamen et al. | 600/438 |
| 2011/0082366 A1 * | 4/2011 | Scully et al. | 600/424 |
| 2011/0178389 A1 * | 7/2011 | Kumar et al. | 600/411 |
| 2011/0258843 A1 * | 10/2011 | Dukesherer et al. | 29/606 |
| 2012/0059249 A1 * | 3/2012 | Verard et al. | 600/424 |

FOREIGN PATENT DOCUMENTS

| | | |
|---|---|---|
| WO | WO0014668 | 3/2000 |
| WO | WO0106924 | 2/2001 |
| WO | WO2007137179 | 11/2007 |

OTHER PUBLICATIONS

Irving Kaplan et al., "Real Time MRI-Ultrasound: Image Guided Stereotactic Prostate Biopsy", Magnetic Resonance Imaging, vol. 20, Issue 3, Apr. 2002 (Abstract).

* cited by examiner

200~# METHOD AND SYSTEM FOR PERFORMING BIOPSIES

CROSS REFERENCE TO RELATED CASES

Applicants claim the benefit of International Application Number PCT/IB2009/052519, filed Jun. 12, 2009, and Provisional Application Ser. No. 61/074,158, filed Jun. 20, 2008.

This invention was made in the performance of a Cooperative Research and Development Agreement with the United States Public Health Service (CRADA No. NCI-NIHCC-01864). The Government of the United States may have certain rights in the invention.

The present application relates to medical procedures, in particular in conjunction with biopsies and will be described with particular reference thereto. However, it is to be appreciated that the exemplary embodiments can also find application in conjunction with other medical procedures, positioning other medical devices, and the like.

Prostate cancer is a major healthcare challenge. In the United States, one out of every six men are affected by the disease during their lifetime. Prostate cancer is second only to lung cancer as a leading cause of cancer death in men.

Today, the most popular prostate cancer screening method is serum prostate-specific antigen screening followed by six or more biopsies under real-time 2D trans-rectal ultrasound guidance. As part of this procedure, the prostate is typically divided into six zones of equal volume. One or more biopsies are obtained from each of the six zones in a systematic, but inherently undirected, fashion. This procedure is called sextant biopsy.

Sextant biopsy is widely used due to its low cost and simplicity relative to other methods of detecting prostate cancer. However, sextant biopsy has been shown to have a significant false negative rate and may be inaccurate with regard to the actual location of a biopsy. The results of sextant biopsy are commonly reported using a crude standard map of the prostate on which biopsy results are manually annotated by the pathologist. This map is inherently inaccurate because the actual site of the biopsy is unknown to the annotating pathologist.

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In accordance with one aspect of the exemplary embodiments, a method can include providing a probe with a deployable biopsy needle; registering a tracking system with diagnostic images; acquiring an image of a target region of a patient using the imaging system; performing a biopsy procedure of the target region; obtaining ultrasound imaging of the target region during the biopsy procedure; acquiring tracking information for a location of at least one of the biopsy needle and the probe during the biopsy procedure; marking a biopsy site for the biopsy procedure on the ultrasound imaging; and transforming the biopsy site from the ultrasound imaging to the diagnostic images based on the tracking information and the registration of the tracking system with the diagnostic images.

In accordance with another aspect of the exemplary embodiments, a computer-readable storage medium can include computer-executable code stored therein, where the computer-executable code is configured to cause a computing device in which the computer-readable storage medium is loaded to execute the steps of registering a tracking system with diagnostic images where the tracking system is capable of tracking at least one of a probe, a biopsy needle deployable from the probe, and a needle guide operably connected with the probe; obtaining ultrasound imaging of a target region and acquiring tracking information for a location of at least one of the probe, the biopsy needle and the needle guide during a biopsy procedure; and transferring a marking of a biopsy site associated with the biopsy procedure from the ultrasound imaging to the diagnostic images based on the tracking information and the registration of the tracking system with the diagnostic images.

In accordance with another aspect of the exemplary embodiments, a biopsy system can include an imaging system for obtaining diagnostic images of a target region; a tracking system; a probe having a deployable biopsy needle for performing a biopsy procedure where the tracking system generates tracking information for at least one of the probe and the biopsy needle; an ultrasound imaging system for obtaining ultrasound imaging of the target region; and a computer in communication with the tracking system, the imaging system and the ultrasound imaging system. The computer can register the tracking system with the diagnostic images, and the computer can transfer a marking of a biopsy site associated with the biopsy procedure from the ultrasound imaging to the diagnostic images based on the tracking information and the registration of the tracking system with the diagnostic images.

In accordance with another aspect of the exemplary embodiment, a system can fuse MRI images and real-time Trans-rectal Ultrasound (TRUS) images during targeted prostate biopsies to combine the advantages of the sensitivity of MRI with the real-time imaging capabilities of ultrasound. The image fusion between previously acquired MRI images and real-time TRUS images can be performed using electromagnetic tracking, which allows the position and orientation of the ultrasound probe to be determined within the human body (e.g., an in vivo global positioning system). As the prostate is scanned with ultrasound, the system can overlay the corresponding multi-planar reconstructions of the MRI and superimpose them on the ultrasound image. Image-based registration can be carried out in real time to compensate for prostate motion.

The exemplary embodiments described herein have a number of advantages over contemporary systems and processes, including accurate mapping of biopsy sites.

The above-described and other features and advantages of the present disclosure will be appreciated and understood by those skilled in the art from the following detailed description, drawings, and appended claims.

Figure 1:
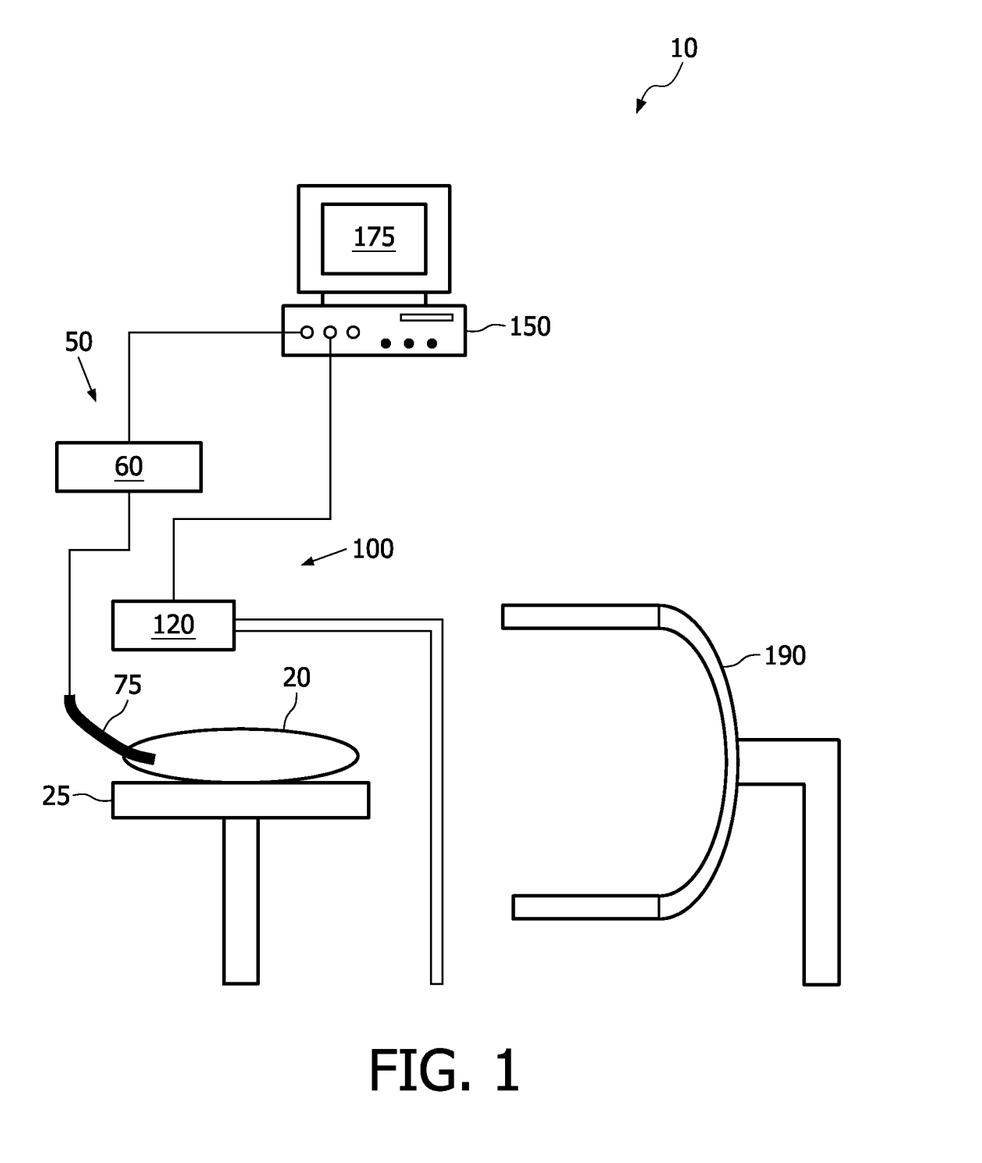
FIG. 1 is a schematic illustration of an exemplary embodiment of a system for use in biopsies.
Figure 2:
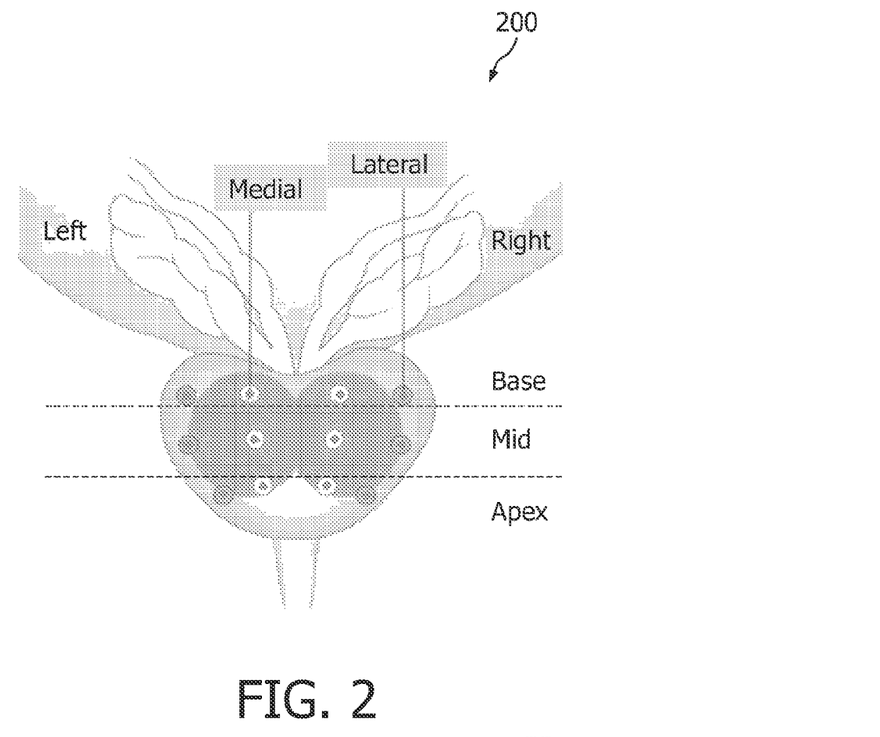
FIG. 2 is a schematic illustration of a prostate region for performance of the biopsy.

Referring to the drawings, and in particular to FIGS. 1 and 2, a detection system 10 can have an ultrasound imaging system 50, a tracking system 100 and an imaging system 190 that can be utilized for obtaining mapping of biopsy positions or sites in a target region of a patient 20. The exemplary embodiments are described herein with respect to biopsies performed on a prostate gland 200 as shown in FIG. 2. However, it would be understood by one of ordinary skill in the art that the exemplary systems and methods described herein can be utilized with respect to various parts of the body, human or otherwise, including organs, tissue, and so forth.

Each of these systems 50, 100 and 190 can be in communication with a computer 150 having a display device 175 (e.g., a monitor) connected thereto. The computer 150 can be various types and can include various components, including multiple processors for parallel processing via a workstation. However, while the exemplary embodiment describes each of the systems 50, 100 and 190 being connected to the computer 150, it would be understood by one of ordinary skill in the art that certain techniques that are described with respect to system 10 can be performed independently of other techniques. For example, the imaging system 190 can be an independent system that obtains images of the target region of the patient 20 before or after the biopsy procedure, where the imaging system 50 and the tracking system 100 are employed for the further techniques that are utilized by system 10 for the mapping of the biopsy sites.

Figure 3:
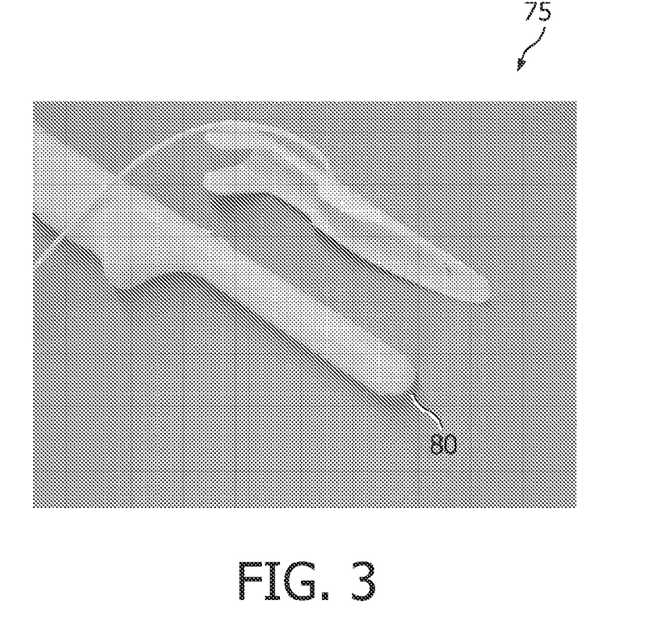
FIG. 3 is a schematic illustration of a biopsy probe for use with the system of FIG. 1.

Referring additionally to FIG. 3, the ultrasound imaging system 50 can be in communication with the computer 150 and can include an ultrasound controller 60 and an ultrasound probe 75. The particular type of ultrasound controller 60, probe 75 and other ultrasound components that are utilized by system 10 can vary, and the particular imaging techniques, such as with respect to data capture, analysis and presentation, can also vary. For example, the probe 75 can be a TRUS probe having a needle guide for deploying the biopsy needle from the TRUS probe. The particular type and configuration of the TRUS probe 75, including the needle guide and deployable biopsy needle, can also vary. The present disclosure also contemplates the use of other types of ultrasound probes along with other types of biopsy devices, which allow for obtaining ultrasound images of the biopsy device while tracking the device, as will be described again later.

In one embodiment, the controller 60 can include a beamformer for processing received echo signals, a Doppler processor for processing Doppler-related information, and an image processor for forming 2D and/or 3D images. The controller 60 can also include a memory device, such as a CINELOOP® memory, and a video processor. In another embodiment, the controller 60 can include components and/or utilize techniques associated with steering and electronic focusing of the ultrasound waves of the probe 75. Other components and/or techniques can also be used with the controller 60, such as an automatic border detection processor that can define and graphically overlay anatomical borders with respect to the images presented. The present disclosure also contemplates the use of other components and/or techniques in addition to, or in place of, the components of controller 60 described above. It should further be understood by one of ordinary skill in the art that controller 60 or one or more of its components can be incorporated into, or shared with, computer 150, such as for data processing and presentation techniques.

The tracking system 100 can be in communication with the computer 150 and can include a field generator 120, such as positioned above a bed 25 or other support for the patient 20. However, the particular positioning of the field generator 120 can vary depending on a number of factors, including the type of field generator or the structure of the other components of system 10 (e.g., use of a C-arm x-ray device). For instance, the field generator 120 can be positioned under the bed 25 and affixed thereto. The field generator 120 can be in communication with one or more sensors 80 connected to, or otherwise integrated with, the TRUS probe 75, to allow for tracking of the probe by tracking system 100. The sensors 80 can be various types depending on a number of factors, including the type of tracking technique that is being utilized.

In one embodiment, the tracking system 100 can be an electromagnetic tracking system that utilizes an electromagnetic field generator 120 and one or more electromagnetic sensors 80 coupled to, or incorporated in, the TRUS probe 75. Other components can be utilized by the system 100, such as fiducial markers. In one embodiment, the tracking system 100 can use various tracking components, such as those available from Traxtal Inc. or Northern Digital Inc. As another example, the tracking system 100 can utilize optical tracking techniques and components, such as available in the Northern Digital Optotrak Certus Motion Capture System. Other techniques and components can be used as a location sensor or transmitter and a location monitor or receiver for tracking the position of the TRUS probe 75, including ultrasound registration techniques and components. In another embodiment, the tracking sensors 80 can be connected to, or otherwise integrated with, the needle guide of the TRUS probe 75 and/or the biopsy needle.

Imaging system 190 can utilize various modalities of imaging. In one embodiment, imaging system 190 can utilize Magnetic Resonance Imaging (MRI). The present disclosure contemplates the use of other modalities of imaging or combinations of imaging modalities by the imaging system 190, including Computed Tomography (CT), contrast ultrasound, positron emission tomography (PET), Single Photon Emission Computed Tomography (SPECT), and so forth.

Referring additionally to FIGS. 4-14, a method that may be utilized for performing biopsies with system 10 is shown and generally represented by reference numeral 400. It should be understood by one of ordinary skill in the art that the steps described with respect to method 400 are intended to be exemplary of the use of system 10 and more or less steps can be employed, including the steps that are shown with broken lines. Additionally, other components or devices that are not specifically described with respect to system 10 can also be employed in the performance of method 400.

Figure 4:
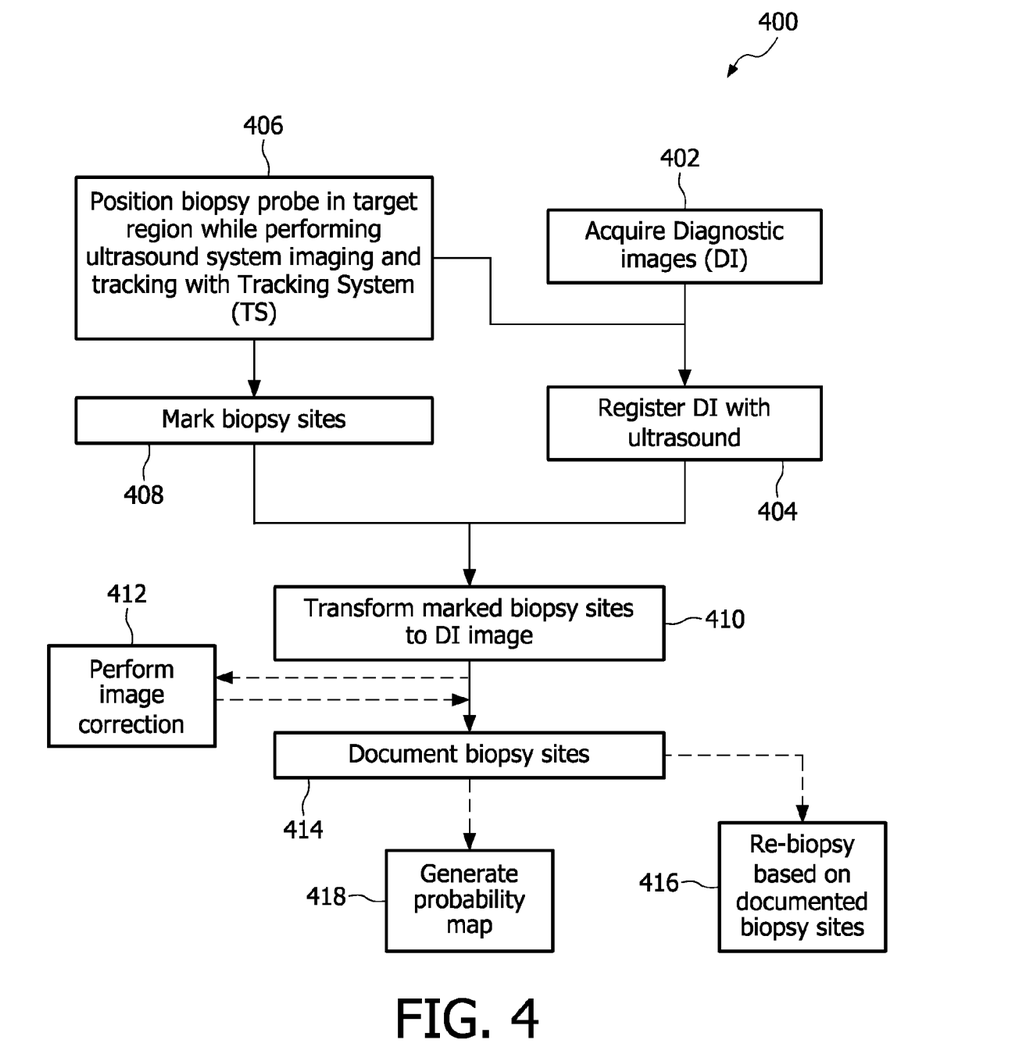
FIG. 4 is a method that can be used by the system of FIG. 1 for performing a biopsy.
Figure 5:
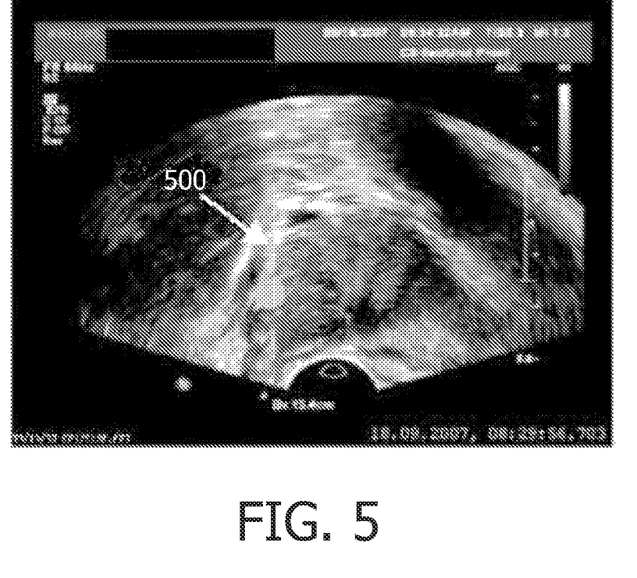
FIG. 5 depicts an ultrasound image generated by the system of FIG. 1 with a marked biopsy site.

Method 400 can include step 402, where diagnostic images of the prostate region or other targeted biopsy area can be acquired using the imaging system 190. In step 404, the tracking system 100 can be registered with the diagnostic images. The registration technique can include one or more calibration steps as are known in the art, such as through acquiring position data while maintaining the tracking system components in a stationary position. For instance, the registration technique can include each point acquired by the tracking system 100 corresponding to a respective point in the image data acquired by the imaging system 190.

In step 406, a biopsy procedure, such as a sextant prostate biopsy, can be performed using the TRUS probe 75 while obtaining and storing real-time ultrasound images with the synchronized tracking information for the probe (or biopsy needle or needle guide). Where the biopsy needle is deployed through the needle guide of the TRUS probe 75, the alignment of the biopsy needle with the ultrasound image plane can be maintained. The ultrasound imaging allows for identification of the biopsy needle in the imaging.

In step 408, the biopsy site or position can be marked. For instance, a biopsy needle is recognizable, and can be designated with mark 500, in FIG. 5. The marking can be performed in real-time and/or can be performed retrospectively using recorded ultrasound images. In one embodiment, image-processing algorithms (e.g., needle recognition techniques) can be utilized to determine the needle position and mark the biopsy site without the need for intervention by the clinician. The biopsy site marking can be performed by system 10 in real-time and/or retrospectively. In another embodiment, system 10 can provide a mark with the shape of the biopsy sample (e.g., cylindrical) to designate the biopsy site. For example, the biopsy mark shape can be based on the known biopsy needle type.

Figure 6:
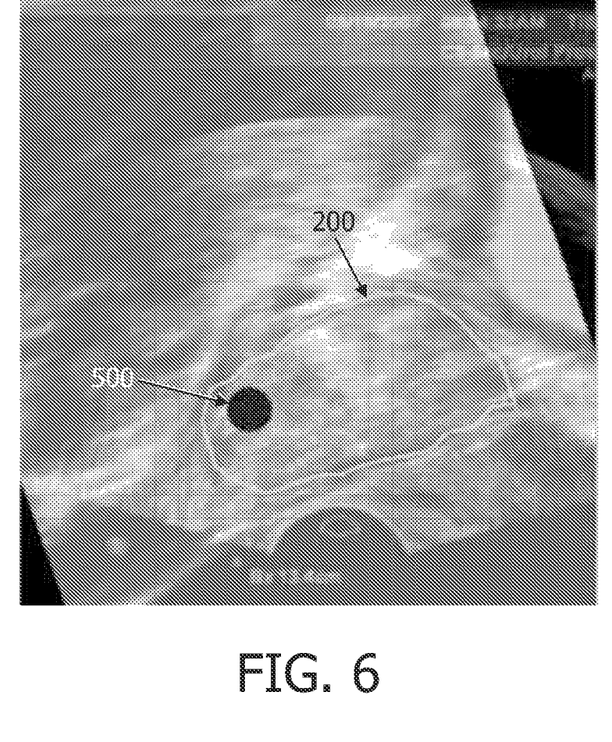
FIG. 6 depicts an image generated by the system of FIG. 1 with a fusion of Magnetic Resonance Imaging (MRI) and ultrasound imaging.
Figure 7:
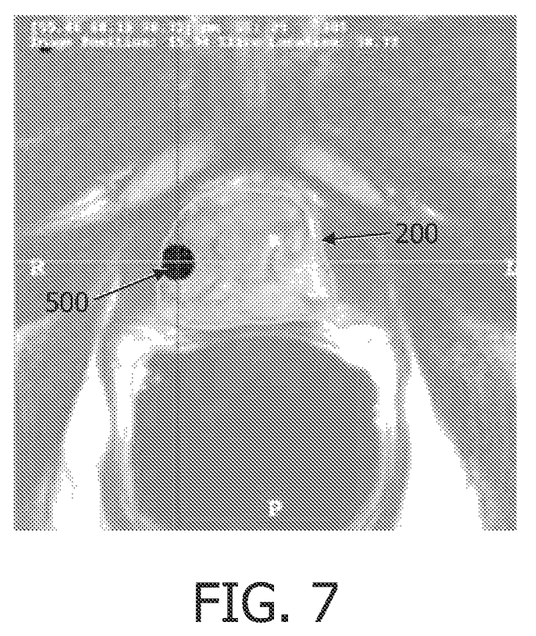
FIG. 7 depicts an MRI image of an axial view generated by the system of FIG. 1 with the marked biopsy site.
Figure 8:
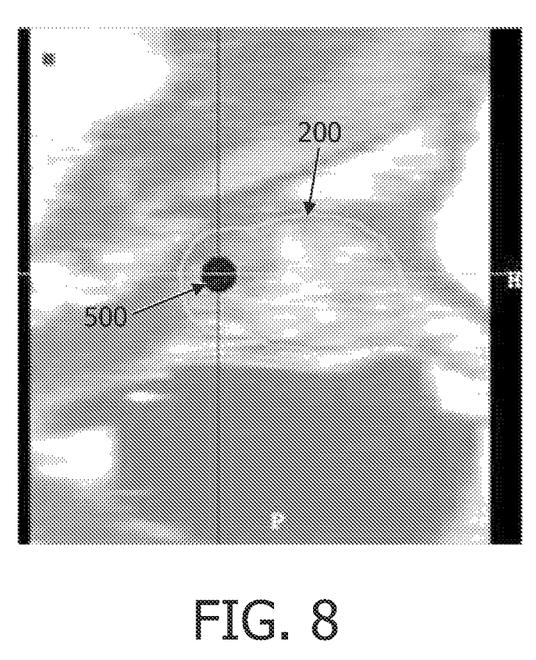
FIG. 8 depicts an MRI image of a sagittal view generated by the system of FIG. 1 with the marked biopsy site.
Figure 9:
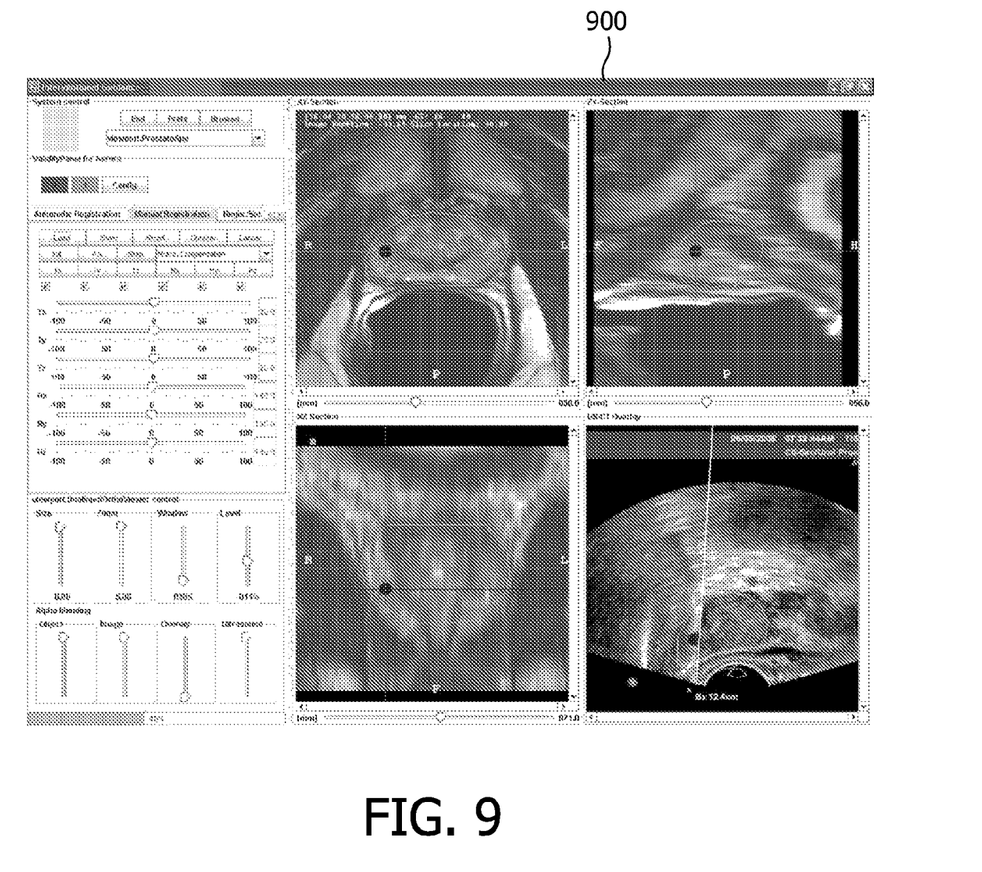
FIG. 9 depicts a Graphical User Interface (GUI) of the system of FIG. 1 with a registration of the ultrasound imaging and MRI imaging.
Figure 10:
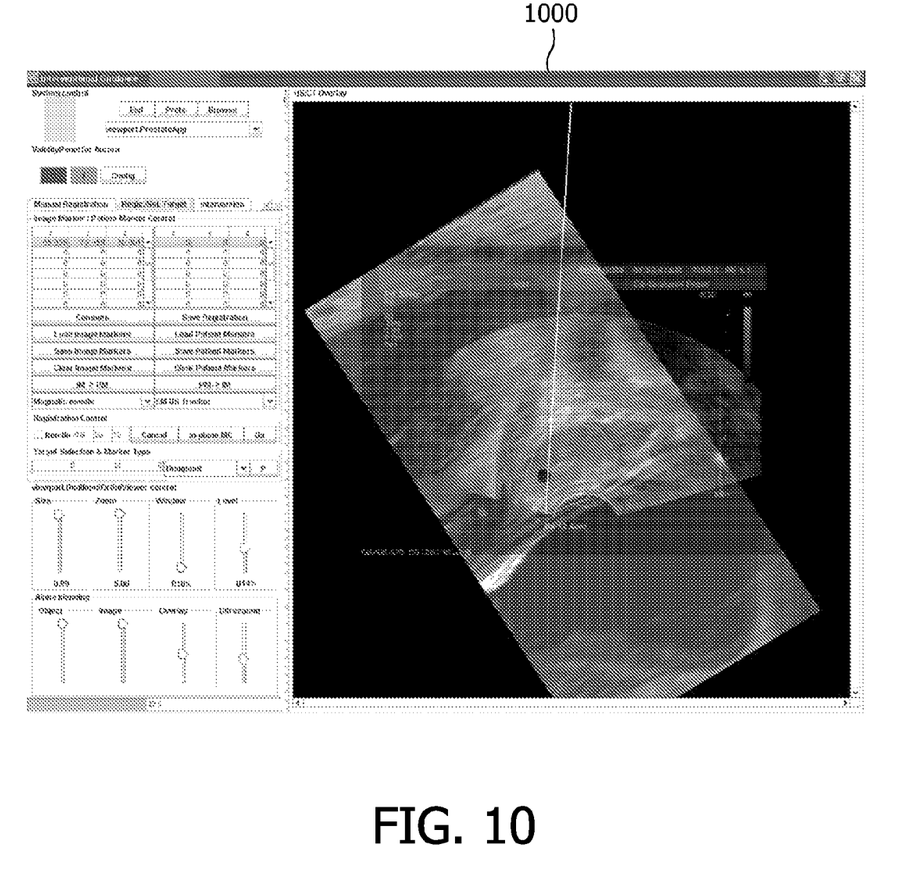
FIG. 10 depicts a GUI of the system of FIG. 1 with an overlay of the ultrasound imaging and MRI imaging.
Figure 11:
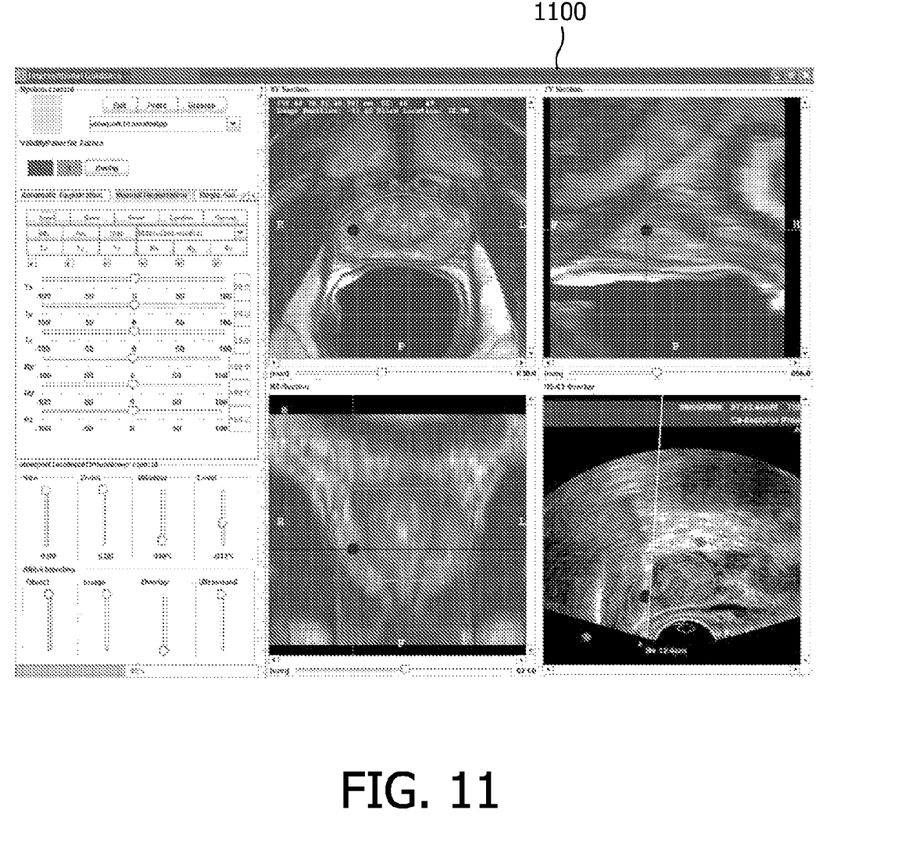
FIG. 11 depicts a GUI of the system of FIG. 1 with biopsy location mapping transformed to the MRI imaging.

In step 410 and as shown in FIG. 6, system 10 can fuse, overlay or otherwise merge the ultrasound imaging with the MRI imaging based on the recorded tracking information from the tracking system 100 and the registration between the MRI image and the tracking system obtained during the biopsy procedure. The marked biopsy sites can then be transformed to the diagnostic MRI image (e.g., transferred to the corresponding position on the MRI image) as shown in the axial and sagittal views of FIGS. 7 and 8. In one embodiment in step 412, image correction techniques can be applied to the acquired data to provide for a more accurate image fusion or merging. For instance, image-based motion/deformation correction algorithms can be applied by computer 150 to the acquired data to account for image misalignment due to prostate motion. System 10 can provide various Graphical User Interfaces (GUI) for presenting the images and information obtained by method 400. For instance, GUI 900 of FIG. 9 can allow a clinician to manually register probe 75 with the imaging system 190. GUI 1000 can allow a clinician to fuse or overlay the MRI imaging with the ultrasound imaging. GUI 1100 can allow a clinician to map the biopsy locations onto the MRI imaging.

Figure 13:
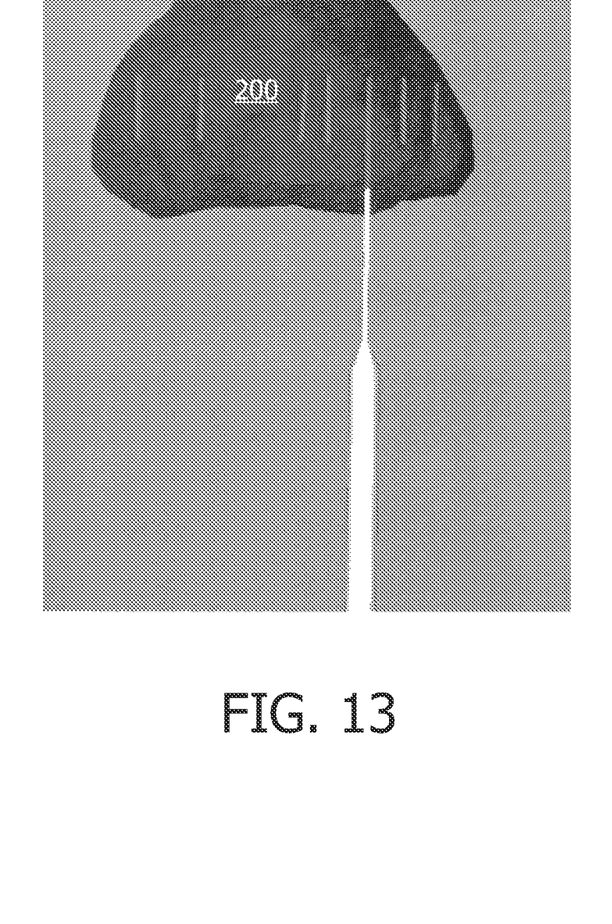
FIG. 13 depicts an image generated by the system of FIG. 1 showing biopsies documented with a 3D TRUS.
Figure 14:
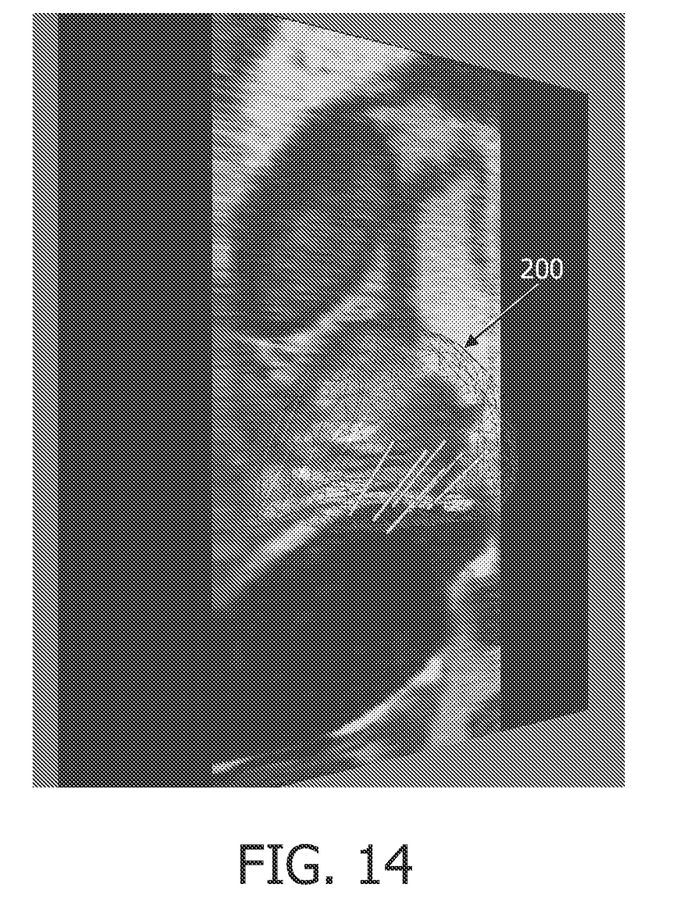
FIG. 14 depicts an image generated by the system of FIG. 1 showing biopsies documented with MRI.

In step 414, the marked biopsy sites are thus accurately located and preserved for documenting the location of the biopsy procedure. The biopsy sites can be documented in the MRI image and/or the reconstructed 3D TRUS image as shown in FIGS. 13 and 14. The documenting of the biopsy sites can be utilized in a number of ways, including validation techniques such as correlating the results of pathologic examinations with the corresponding locations of the MRI image, in order to provide the ground truth for image-based cancer detection on these locations. In one embodiment in step 416, the documented biopsy sites can be utilized as a reference to plan future targeted re-biopsies, such as where the biopsy results of a patient are negative but the patient continues to have high PSA levels.

In another embodiment in step 418, the documented biopsy sites can be utilized to generate a statistical cancer distribution map which can assist in improving biopsy procedures for other patients. For instance, a distribution map of the locations of prostate cancer can be generated by registering the biopsy sites of a number of patient studies to a common coordinate system. In one embodiment, the biopsy site can be based on the coronal plane since each biopsy is a linear core of tissue sample (e.g., approximately 15 mm long) which is typically obtained in the anterior-posterior direction. Each of the patient's prostate surfaces can be manually segmented in the MRI image and projected to the coronal plane. The two dimensional (2D) boundary of each projected prostate can be deformed to match a 2D model in the coronal plane. The image registration between each patient study and the model is thus established. The biopsy sites of each patient study can then be transformed to the 2D model, allowing a cancer distribution map to be constructed based on the results of the sextant biopsies. In another embodiment, a 3D distribution map can be generated using deformable image registration between the image of each patient study and a 3D model.

EXAMPLE

Figure 12:
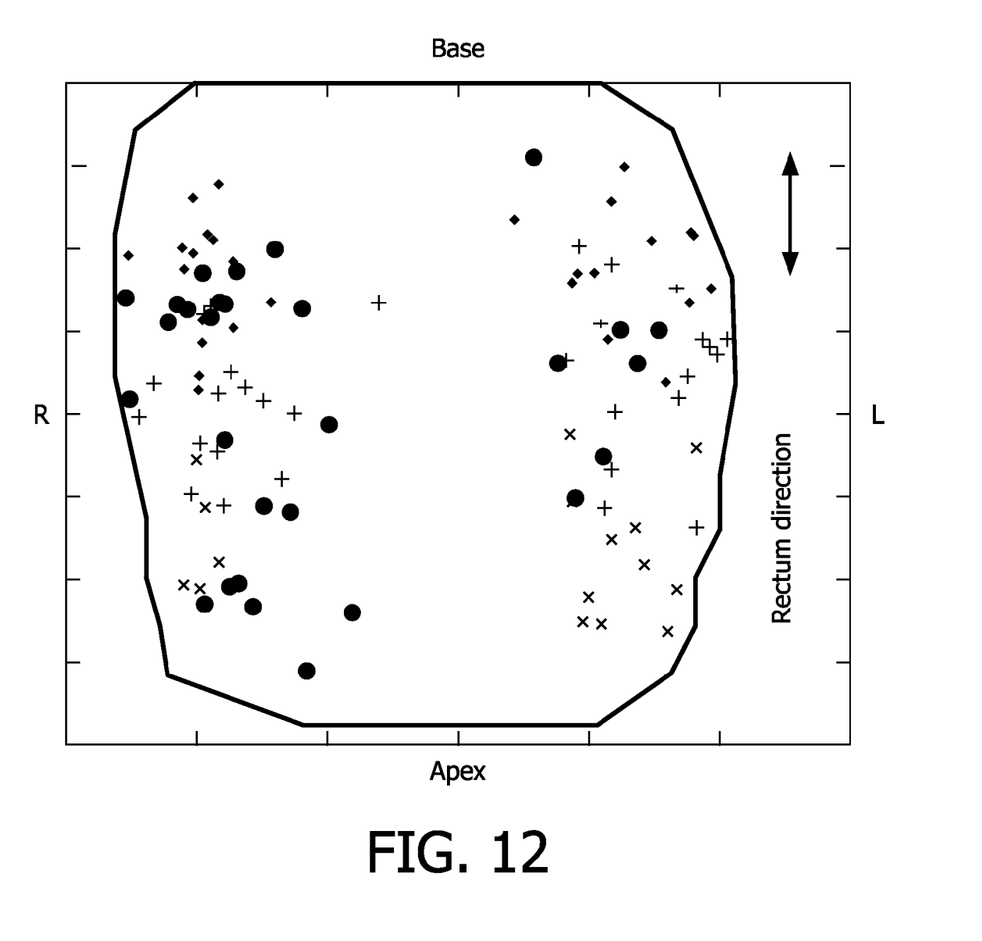
FIG. 12 represents the results of sextant biopsy procedures for ten patient studies using the system of FIG. 1.

Applicants retrieved data based on the performance of six to twelve-core prostate biopsies of ten patients. The biopsy procedures were performed using the methodology and systems described with respect to the exemplary embodiment. FIG. 12 shows the biopsy results of the ten patients. The circles show the positions of positive biopsies as confirmed by pathological examination. The positions of negative biopsies, as confirmed by pathological examination, at the base, mid and apex regions are shown by "·", "+" and "×", respectively. A probability map of prostate cancer can be constructed by computing the histogram of the distribution.

System 10 and method 500 can be utilized to establish a correlation between diagnostic images and tumor histology. With sufficient accuracy, this correlation can provide ground truth to physicians and/or computer aided diagnosis algorithms for validation of image-based cancer detection. A statistical cancer distribution map can be constructed based on biopsy results, helping to optimize conventional biopsy procedures based on prior probability. Over 700,000 prostate biopsies are performed in the U.S. alone, so that method 500 can be provided with a large number of patient samples for constructing a prostate cancer probability map that may lead to more accurate detection of prostate cancer. In another embodiment, the correlation between the diagnostic images and the pathological examination can be utilized for training of clinicians and/or image processing algorithms in the detection of prostate cancer, such as through proper positioning of the biopsy needle during biopsy procedures.

In one embodiment, computer 150 can provide post-procedural data to a database residing on a hospital information system infrastructure (e.g., the data being in DICOM-RT format). The hospital information system can send the data to a processor so that the data can be used to guide a second medical procedure on the same patient. In another embodiment, the hospital information system can aggregate the data and generate a statistical analysis across a plurality of patients. The hospital information system can transfer the statistical analysis to a processor, where the statistical analysis is used to guide a medical procedure. In another embodiment, the hospital information system can combine the statistical analysis with a patient's medical images to generate a patient specific target map, where the target map is communicated to a processor and the target map is used to guide a medical procedure.

The present disclosure provides a method and system that can be used for real-time targeted prostate biopsy and therapy. The present disclosure provides a method and system that can be used to document the location of biopsy procedures and retrospectively validate image-based cancer detection by correlating the pathologic analysis of biopsy specimens with diagnostic image information (e.g. MRI).

In one embodiment, the distribution of the tissue samples retrieved by system 10 can be utilized for assessing the reliability and sampling error inherent to the ultrasound transducer that is being utilized. The distribution map can reflect the integrity of the sampling methodology from transducer to image to tracking to patient. For instance, the tissue map of FIG. 12 shows higher rates of diagnosis and more evenly distributed biopsies, which may be reflective of the particular ultrasound transducer that is being used. In another embodiment, the distribution of the tissue samples retrieved by system 10 can be utilized for assessing the reliability and sampling error inherent to the particular patient position (e.g., left side down decubitus). For instance, the right side targeting can be more intuitive and natural or comfortable to the operator (e.g., right side up is easier to do hand-to-eye coordination and ergonomics) versus left side down where the transducer is flipped and the biopsy gun inserted at an opposite and rotated orientation. The prostate may also sit differently related to gravity. In one embodiment, the particular positioning of the patient 20 can be adjusted to optimize the data collected, such as doing an MRI in left side down decubitus to minimize gravity or positional effects. Thus, the methodology and components of system 10, including the distribution map, can be used to evaluate or validate a combination of positions and transducers for diagnostic yield, and ability to efficiently cover the target volumes, such as in the case of random sextant biopsies. Efficient coverage can lead to better diagnostic yield in terms of higher sensitivity.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A method of using a tracking system for performing a biopsy, the method comprising acts of:
    providing a probe with a deployable biopsy needle;
        acquiring diagnostic images of a target region including a biopsy site;
        registering the tracking system with the diagnostic images;
        obtaining ultrasound images of the target region during the biopsy;
        the tracking system acquiring tracking information for a location of at least one of the biopsy needle and the probe during the biopsy;
        marking the location at the biopsy site on the ultrasound images; and
        transforming the location at the biopsy site from the ultrasound images to the diagnostic images based on the tracking information and the registration of the tracking system with the diagnostic images.

2. The method of claim 1, wherein the tracking system is an electromagnetic tracking system, and at least one of the probe and the biopsy needle comprises one or more electromagnetic sensors.

3. The method of claim 1 wherein the target region is a prostate and the diagnostic images are acquired by a magnetic resonance imaging system and further comprising an act of displaying an MRI image showing the biopsy site on a computing device.

4. The method of claim 1, wherein the act of:
    marking of the location at the biopsy site on the ultrasound images is performed in real-time; and
    further comprising an act of using the diagnostic images having the marked location at the biopsy site thereon for performing an additional medical procedure.

5. The method of claim 1, further comprising acts of:
    acquiring the locations at the biopsy sites for a plurality of patients;
    associating the locations at the biopsy sites with a common coordinate system; and
    generating a distribution map using the common coordinate system.

6. The method of claim 5 further comprising acts of:
    training at least one clinician to perform the biopsy using the distribution map; and using a correlation between the diagnostic images and pathological examination in an image processing algorithm for detection of cancer.

7. The method of claim 1, further comprising an act of performing imaging correction to account for motion of the target region.

8. The method of claim 1, further comprising an act of adjusting at least one of an ultrasound transducer type and a patient position during a medical procedure based on the diagnostic images having the marked location at the biopsy sites.

9. A non-transitory computer-readable storage medium for storing computer-executable code configured to cause a computing device in which the computer-readable storage medium is loaded to execute a method of using a tracking system for performing a biopsy, the method comprising acts of:
  acquiring diagnostic images of a target region including a biopsy site;
  registering the tracking system with the diagnostic images;
  obtaining ultrasound images of the target region during the biopsy;
  the tracking system acquiring tracking information for a location of at least one of the probe, the biopsy needle and the needle guide during a biopsy; and
  transferring a marking of the location at the biopsy site from the ultrasound images to the diagnostic images based on the tracking information and the registration of the tracking system with the diagnostic images.

10. The computer-readable storage medium of claim 9, further comprising an act of marking the location at the biopsy site on the ultrasound images.

11. The computer-readable storage medium of claim 9 further comprising an act of detecting a position of the biopsy needle based on the ultrasound imaging and defining the marking of the location at the biopsy site based on the detected position.

12. The computer-readable storage medium of claim 9, wherein the diagnostic images are generated using at least one of magnetic resonance imaging, computed tomography, contrast ultrasound, positron emission tomography, and single photon emission computed tomography.

13. The computer-readable storage medium of claim 9 further comprising an act of generating a map distribution comprising the marked locations at the biopsy sites for a plurality of patients.

14. The computer-readable storage medium of claim 9 further comprising an act of displaying the marking of the location at the biopsy site on the diagnostic images using a shape corresponding to a biopsy sample obtained by the biopsy needle.

15. A biopsy system comprising:
  an imaging system for acquiring diagnostic images of a target region including a biopsy site;
  a probe having a deployable biopsy needle for performing a biopsy procedure;
  a tracking system for acquiring tracking information for a location of at least one of the probe and the biopsy needle;
  an ultrasound imaging system for obtaining ultrasound images of the target region; and
  a computer in communication with the tracking system, the imaging system and the ultrasound imaging system, configured the tracking system with the diagnostic images acquired by the imaging system, and
  configured to transfer a marking of the location at the biopsy site associated with the biopsy procedure from the ultrasound images to the diagnostic images based on the tracking information and the registration of the tracking system with the diagnostic images.

16. The system of claim 15, wherein the tracking system is an electromagnetic tracking system, and wherein at least one of the biopsy needle and the probe comprises one or more electromagnetic sensors.

17. The system of claim 16, wherein the probe is a transrectal ultrasound probe having a needle guide for deploying the biopsy needle, and wherein the ultrasound imaging is obtained using the TRUS probe.

18. The system of claim 15, wherein the computer retrieves the marking of the location at the biopsy site in real-time.

19. The system of claim 15, wherein the imaging system is one of a magnetic resonance imaging system, a computed tomography system, a contrast ultrasound system, a positron emission tomography system, and a single photon emission computed tomography system.

20. The system of claim 15, wherein the computer generates a map distribution comprising marked biopsy sites for a plurality of patients.

* * * * *